United States Patent [19]

Schal

[11] Patent Number: 5,616,248
[45] Date of Patent: Apr. 1, 1997

[54] METHOD FOR THE PREPARATION OF HEMODIALYSIS FLUIDS CONTAINING BICARBONATE

[76] Inventor: Wilfried Schal, Tannenwaldweg 27, 61350, Bad Homburg, Germany

[21] Appl. No.: 88,734

[22] Filed: Jul. 8, 1993

Related U.S. Application Data

[63] Continuation-in-part of Ser. No. 43,309, Apr. 6, 1993, abandoned.

[30] Foreign Application Priority Data

Apr. 6, 1992 [DE] Germany ............................ 42 11 455.1
Feb. 19, 1993 [DE] Germany ............................ 43 05 101.4

[51] Int. Cl.⁶ ............................ A61K 9/00; A61K 33/00; A61K 33/10; B01D 61/30
[52] U.S. Cl. ............................ 210/647; 210/646
[58] Field of Search ............................ 210/646, 647, 210/321.71; 252/1; 514/832

[56] References Cited

U.S. PATENT DOCUMENTS

| | | | |
|---|---|---|---|
| 4,202,760 | 5/1980 | Storey et al. ............... | 210/321.71 |
| 4,489,535 | 12/1984 | Veltman ............... | 252/1 |
| 4,756,838 | 7/1988 | Veltman ............... | 210/647 |
| 4,770,769 | 9/1988 | Schael ............... | 210/929 |
| 5,091,094 | 2/1992 | Veech ............... | 210/647 |
| 5,122,516 | 6/1992 | Watanabe et al. ............... | 210/647 |
| 5,244,568 | 9/1993 | Lindsay et al. ............... | 210/647 |

*Primary Examiner*—John Kim
*Attorney, Agent, or Firm*—Oblon, Spivak, McClelland, Maier & Neustadt, P.C.

[57] ABSTRACT

In the method for the preparation of bicarbonate-containing hemodialysis fluids of individually adaptable compositions according to specific therapeutic requirements of patients a combination of a quantitatively greatly predominating basic concentrate of uniform standard composition is applied in conjunction with an individually selected additional or individual concentrate. The basic concentrate, mainly consisting of sodium chloride and sodium bicarbonate, supplies to the dialysis fluid a sodium concentration at or slightly below the lower limit of the physiological range, whereas the individual concentrate supplies the complementary concentration of sodium up to an individually selected physiological level as well as salts of potassium, calcium, and magnesium and also glucose in individually adapted concentrations. The individual concentrate is a 120- to 250-fold liquid concentrate, resulting in an easy to handle quantity of typically one liter for one dialysis treatment.

14 Claims, 4 Drawing Sheets

METHOD FOR THE PREPARATION OF HEMODIALYSIS FLUIDS CONTAINING BICARBONATE

This is a continuation-in-part application of application Ser. No. 08/043,309, filed on Apr. 6, 1993, now abandoned.

BACKGROUND OF THE INVENTION

The invention relates to a method for the preparation of hemodialysis fluid containing bicarbonate ions. For one hemodialysis treatment approximately 120–180 liters of dialysis fluid are required, a typical composition of which is as follows:

| Component | Concentration (mmol/liter) |
|---|---|
| $Na^+$ | 139 |
| $K^+$ | 2.5 |
| $Ca^{++}$ | 1.65 |
| $Mg^{++}$ | 0.6 |
| $Cl^-$ | 111 |
| $HCO_3^-$ | 32 |
| acetate$^-$ | 3 |

The problems in selecting a suitable composition of the dialysis fluid, adapted to the physiological requirements, are, for example, discussed in the publication "Replacement of Renal Function by Dialysis" (Editor: W. Drukker, F. M. Parsons, J. F. Maher; Martinus Nijhoff Medical Division, Den Haag 1978) in the chapter "The Composition of Dialysis Fluid" (Author: F. M. Parsons, A. M. Davison). More recent information is found in the book "Blutreinigungsverfahren" ["Methods of blood purification"] (Editor: H. E. Franz, 4th Edition; Georg Thieme Verlag; Stuttgart, N.Y., 1990) and the literature cited therin. It is well known and also apparant from these publications, that to adapt the composition of dialysis fluids to the individual state of disease of each single patient is one of the main requirements for an optimization of hemodialysis treatment.

This question requires increased attention with regard to patients suffering from additional acute or chronic diseases, while also considering children, elderly and weak patients, and cases of acute renal failure. In these cases it is frequently necessary to correct the composition of the dialysis fluid on the basis of actual diagnostic results and taking into account the additional therapeutical measures applied. But also for the "normal" patient the composition should be carefully adapted in order to prevent long-term damages.

The technical means for an individual adaptation of dialysis fluids are however still inadequate. There is no system available which would be easy to handle and solve the problem at an acceptably low cost and with simple technical equipment.

The occurence of negative dialysis side-effects may be reduced by changing the concentration of certain constituents of the dialysis fluid in the course of a treatment session continuously or in discrete steps. This method is known as "profiling" a dialysis fluid. With respect to cardiovascular instabiliy it has been found especially advantageous to apply a high sodium concentration (e.g. 150 mmol/liter) in the first phase and a low sodium concentration (e.g. 130 mmol/Liter) in the final phase. For patients with a high blood potassium level, particularly in cases of acute renal failure, a quick reduction of the potassium level may be dangerous. It is therefore recommended to use a dialyis fluid of high potassium concentration initally and to reduce the potassium level in steps down to zero until the end of the session.

Procedures of this kind, deemed important from the medical point of view, are not sufficiently supported by existing methods and equipment.

DESCRIPTION OF THE PRIOR ART

Due to different physiological requirements, dialysis fluids of different compositions are in use. The content of sodium, potassium, calcium, and magnesium salts, for example, may vary within the following ranges (concentrations in mmol/liter):

| | |
|---|---|
| $Na^+$ | 130–150 |
| $K^+$ | 0–5 |
| $Ca^{++}$ | 0.3–2.5 |
| $Mg^{++}$ | 0–1.2 |
| Glucose | 0–15 |

In the literature there are suggestions also to include other substances, e.g. amino acids.

Because of the large quantity of dialysis fluid required for a typical treatment of 4 to 6 hours, it is common practice to prepare the dialysis fluid at the location of its application by diluting commercially available dialysis concentrates with water. For this purpose, hemodialysis machines are equipped with a proportioning device, which mixes concentrate(s) and water in a volumetric ratio as prescibed.

With dialysis fluids of a composition as indicated there is a general problem that calcium and magnesium in conjunction with bicarbonate tend to form insoluble precipitates, the result being that the solution will not remain stable for extended periods of time. This tendency is even more pronounced at higher concentration levels, i.e. if one tries to produce a concentrate of such a dialysis solution. To overcome this problem, there are two different methods in practical use.

I) Acetate Dialysis:

The whole quantity of bicarbonate is replaced by acetate. Because acetate, in conjunction with calcium and magnesium, does not form unsoluble precipitates in the range of concentrations under consideration, all components of the solution can be combined in a single concentrate. Most of the commercially available concentrates for acetate hemodialysis are 35-fold, i.e. they must be diluted with water to the 35-fold of their initial volume, in order to obtain the dialysis solution ready for use. An advantage of these acetate concentrates resides in the fact that they are self-sterilizing.

The replacement of the total bicarbonate by acetate is however unphysiological. For this reason, acetate dialysis, in the past established as a standard method and still not out of use, according to present medical standards is regarded as less than optimum.

II) Bicarbonate Dialysis:

Instead of one single concentrate, two separate concentrates are used, one containig the bicarbonate portion and the other containing the calcium and magnesium portion (together with other constituents in both cases). These two concentrates are separately supplied to the hemodialysis machine and separately proportioned and diluted with water and combined to the final dialysis fluid. The risk of formation of carbonate precipitates with this method exists only after the components have been mixed. With of the high degree of dilution and the correct adjustment of the pH value, obtained by the addition of a physiologically acceptable acid, this tendency can however be neglected.

The obligation to use two separate concentrates makes the handling more difficult and, from a technical point of view, represents a severe disadvantage of bicarbonate dialysis against acetate dialysis. Furthermore, the total liquid volume of the concentrates is typically more than twice the volume required for acetate dialysis. To produce 170 liters of dialysis fluid, which is a typical maximum quantity for one dialysis session, acetate dialysis requires approximately 5 liters of concentrate, wheras bicarbonate dialysis requires approximately 11 to 13 liters. The reason for this is the low solubility of sodium bicarbonate compared to sodium acetate. Furthermore, the dual proportioning system necessary for the two concentrates, including the associated monitoring equipment, is more complicated and expensive. In spite of these difficulties, acetate dialysis has gradually been displaced by bicarbonate dialysis because of the medical advantages of the latter.

In the European patent publication 0 022 922 all possible subdivions of the components of a bicarbonate dialysis fluid into two concentrates are considered, taking into account the two fundamental physico-chemical rules already mentioned:

a) One concentrate must contain the total quantity of bicarbonate ions.

b) The other concentrate must contain the total quantity of calcium and magnesium ions required and the total amount of a (physiologically acceptable) acid for pH adjustment.

All other components, especially sodium and potassium chloride, can unrestrictedly be distributed between the two concentrates.

The European Patent EP 0 086 553 discloses a specific subdivision of the solute components, representing a special case of the above-cited general possibilities:

a) The first concentrate contains the total quantities of sodium bicarbonate and sodium chloride and as necessary potassium chloride and glucose.

b) The second concentrate contains only the calcium and magnesium salts and the acid for pH adjustment.

This specific subdivision offers the advantage that only a very small quantity of the second concentrate is required, which is, thus, easy to handle. 150 ml of this concentrate are sufficient for one dialysis tratment. If only the calcium and/or magnesium content of the dialysis fluid has to be modified, it is thus sufficient to change the composition of this small concentrate volume. If, however, the content of sodium or potassium or glucose also has to be varied, which occurs more frequently, then both concentrates must be changed. This is difficult, because the quantity of the first concentrate amounts to typically 12.85 liters.

In EP 0 086 553 there are also cited other compositions of concentrates from U.S. Pat. No. 4,202,760 and publications of the Bio-Systems and Renal Systems companies. In these examples, similar to the first example of EP 0 022 922, part of the sodium chloride is united with the sodium bicarbonate in a first concentrate, whereas the rest of the sodium chloride, together with calcium and magnesium salts and the acid required for pH adjustment, is contained in the second concentrate. The volumetric ratio of the two concentrates, in these cases, is in the range of 2:1 to 1:1. The concentrate volumes are so large that also, according to this prior art, an adaptation to individual physiological requirements is difficult to handle.

In most cases, according to the present practical state of the art, the following combination of concentrates is applied:

(a) a concentrated (8.4 percent=1-molar) solution of sodium bicarbonate commercially designated as "alkaline bicarbonate hemodialysis concentrate". With reference to the usual gross bicarbonate concentration of 35 mmol/l in the final dialysis fluid, this solution represents a 28.57-fold concentrate.

(b) a 35-fold concentrate of the other constituents of the dialysis fluid, named "acidic bicarbonate hemodialysis concentrate" because of its content of acetic acid, although not containing any bicarbonate by itself.

From these commercially available concentrates, for 170 liters of dialysis fluid, a typical maximum quantity for one dialysis session, the following quantities are required: 5.95 liters of the alkaline bicarbonate hemodialysis concentrate plus 4.86 liters of the acidic bicarbonate hemodialysis concentrate, in total 10.81 liters.

The acidic bicarbonate hemodialysis concentrate contains all constituents (salts of sodium, potassium, calcium, and magnesium, and glucose) which are important for a physiological adaptation. Thus, the adaptation may be obtained by a suitable selection of the acidic concentrate. There remains, however, the disadvantage, that this is a relatively large quantity and, therefore, difficult to handle.

A "profiling" of the dialysis fluid, i.e. a variation of the concention, especially of sodium ions, continuously or in intervals, is imperfectly performed by changing the dosage or proportioning factor of the acid concentrate. There is a disadvantage that the concentration of all constituents then varies in the same ratio. Wide variations, for example a decrementation of the potassium level from 4 mmol/l to zero during an acute dialysis, as mentioned before, cannot be achieved in this way. Also many hemodialysis machines do not offer the possibility to change the mixing ratio.

In order to take account of different therapeutical needs, dependent on the individual state of a patient's disease and variable conditions of treatment, the pharmaceutical industry supplies hemodialysis concentrates in a range of different compositions, for acetate hemodialysis as well as for bicarbonate hemodialysis.

For this purpose, the concentrates are commercially available in canisters of, for example, 10 liters, according to the quantity needed for one dialysis treatment. A canister with the type and composition of concentrate, chosen by the physician according to the individual state of the patient and according to therapeutic objectives, is transported and connected to the dialysis machine, the concentrate being taken in by the machine through a hose from the individual canister. In hospitals, the purified water required for the dilution of the concentrate is normally supplied via a central supply system to all machines.

The advantage of the individual adaptation is however available only with great expense:

a) The transport of the rather heavy concentrate canisters (typically 10 kg) requires a considerable effort from the personnel working in a dialysis unit.

b) The storage of a large assortment of different concentrates in these relatively large canisters is difficult and expensive. A dialysis unit with 20 machines typically consumes 200 to 300 canisters of dialysis concentrate per week.

c) For hygienic reasons, residues of concentrates remaining in the canisters after use should normally be discarded. The removal of these residues, which can amount up to as much as 30 percent of the quantity required, is an economic loss and represents a considerable environmental burden.

d) The empty canisters, generally made of high quality thermoplastic material, cannot, according to present standards, be reused for the same purpose. Also, the restitution and recycling of the material is not a very economic procedure.

In view of the problems of handling and storage as described, in many cases dialysis units prefer to use a central concentrate supply. This means that, in parallel with the water supply system, a concentrate supply system is installed with taps at each treatment site to connect the individual dialysis machines. This concentrate supply system is fed from large concentrate containers having a capacity of typically 500 to 1000 liters which are routinely replaced.

In the case of bicarbonate dialysis a dual tubing system is, however, necessary in order to supply the "alkaline" bicarbonate concentrate and the "acidic" concentrate of the other solution constituents to the dialysis machines separately.

A central concentrate supply system prevents the problems of internal transport and storage of concentrates in a dialysis unit. The large concentrate containers are reusable, and only relatively small quantities of residual concentrates have to be discarded.

However, a severe disadvantage resides in the fact that an individual adaptation of the composition to each single dialysis patient's requirements is then no longer possible, because a central supply system allows only for the distribution of one type of concentrate. The physician, in this case, has to choose an "average" composition of concentrate, adapted to the requirements of a hypothetical "average" patient. Because there are very different opinions about the right concentrate compositions for the "average" patient, the pharmaceutical industry is still obliged to produce and to offer a a large variety of different concentrates, also in large containers for central supply systems. Thus, a great deal of the theoretical economic advantages of central concentrate supply systems connot be fully utilized.

OBJECTIVES OF THE INVENTION

A main objective of the present invention is to provide a more flexible and more economic method for the preparation of dialysis fluids, avoiding most of the aforementioned disadvantages.

In particular, the invention is intended to provide a method which greatly simplifies the preparation and application of dialysis fluids, which are individually adapted to the physiological state and therapeutic requirements of each patient.

Another objective is to provide a method of this kind which can be applied using simple and economic dialysis equipment, and/or in conjunction with existing machines of normal design, whithout needing specialized or unconventional and expensive additional equipment.

The invention is also intended to be applicable in conjunction with existig labour-saving central supply installations for dialysis concentrates and in spite of this offer the opportunity to adapt the composition of dialysis fluids to each patient's individual requirements.

Furthermore, an objective of the invention is to provide a simple and economically acceptable method for "profiling" a dialysis fluid, i.e. to modify its composition in steps or continuously during the course of a dialysis treatment.

Other objectives and improvements obtained by the invention may be visible from the description of examples.

SUMMARY OF THE INVENTION

These objectives are mainly achieved by the following characteristics:

1) For the preparation of dialysis fluid there are used:
   (a) a basic concentrate of uniform and standardized composition, mainly containing sodium chloride and sodium bicarbonate, and
   (b) an individually selectable additional concentrate (individual concentrate) containing the other solution components, including an individually selectable portion of sodium chloride which covers the physiological range of sodium concentrations.

2) The basic concentrate supplies at least 80 percent, typically 90 to 95 percent, of the sodium chloride as well as the total quantity of sodium bicarbonate and may contain an addition of sodium acetate for stabilization. It supplies, with reference to the final dialysis fluid, a concentration of sodium ions at, or slightly below, the lower limit of the physiological range, i.e. in the range of 125 to 135 mmol/Liter, preferably 130 mmol/Liter circa.

The molar ratio of the ions supplied by the basic concentrate is in the following ranges: bicarbonate/sodium less than 0.35, acetate/sodium less than 0.03.

3) The preferred basic concentrate is a 15- to 18-fold liquid concentrate.

4) The basic concentrate may, however, also be applied in different forms:
   (a) as two separate liquid concentrates, i.e. essentially concentrated solutions of sodium chloride and sodium bicarbonate, which may contain an addion of sodium acetate, similar to the single basic concentrate,
   (b) as a mixture of the appropriate dry salts in portions, intended to be dissolved in water at the location of its use,
   (c) as a homogeneous mixture of the respective salts shaped to granules or tablets, suitable for quasi-continuous dosing,
   (d) similar to (c), but shaped to pieces of standardized geometric shape (e.g. bars or rods) and of larger size, eventually adapted to the quantity required for one dialysis session.

5) The individual concentrate supplies ions of sodium, potassium, calcium, and magnesium and also glucose according to the following table, which relates to a basic concentrate supplying sodium in a concentration of 130 mmol/liter (in mmol/liter, with reference to the concentrations in the final dialysis fluid):

|  | average value | typical range | maximum range |
| --- | --- | --- | --- |
| sodium ions | 9 | 5 . . . 14 | (0 . . . 25) |
| potassium ions | 2 | 1 . . . 4 | (0 . . . 5) |
| calcium ions | 1.6 | 0.75 . . . 2 | (0.3 . . . 2.5) |
| magnesium ions | 0.6 | 0.4 . . . 1 | (0 . . . 1.2) |
| glucose | 5 | 0 . . . 10 | (0 . . . 15) |

If the basic concentrate supplies a sodium concentration lower/higher than 130 mmol/liter, the difference has to be balanced by a higher/lower sodium concentration in the individual concentrate.

Furthermore, the individual concentrate contains at least one physiologically acceptable acid, preferably hydrochloric acid, in a concentration, refered to the final dialysis fluid, of 1.5 to 4 mmol/liter. The hydrochloric acid may partially, or totally, be replaced by other physiologically acceptable acids, especially acetic acid, but limiting the total concentration of acetate in the final dialysis fluid to a maximum of 5 mmol/liter.

6) The individual concentrate is a 120- to 250-fold liquid concentrate, preferably 170-fold, the volume of the individual concentrate required for one dialysis treatment preferably being supplied in an infusion bag of typically one liter.

7) Alternatively the individual concentrate may be supplied as a prefabricated mixture of its components (without water) in portions intended to be dissolved in water at the location of its use.

8) According to the quantities and solubilities of the solutes, the volumetric ratio of the basic and individual concentrates—if applied as prefabicated liquid concentrates—is in the range of 7:1 to 16:1, typically about 11:1.

9) A dry basic concentrate is dissolved in water in discrete batches or continuously, thus forming a more or less concentrated liquid concentrate, or in conjunction with the solving process, by admixing a higher proportion of water, a more diluded solution is formed, which represents a basic dialysis fluid of final concentration, requiring only the addition of the individual concentrate to obtain the dialysis fluid ready for use.

10) The prefabricated liquid basic concentrate or a basic concentrate obtained by dissolving the dry substance in water or a basic dialysis fluid of final concentration are distributed to a group of dialysis machines from a central supply system.

11) Profiling of the dialysis fluid, i.e. changing its composition in the course of a dialysis session, is obtained by applying different individual concentrates in a sequence or in different ratios in parallel.

DESCRIPTION OF PREFERRED EMBODIMENTS

Example 1.0:

A 15-fold liquid basic concentrate was produced by dissolving in water the following quantities of salts per liter of concentrate:

| | |
|---|---|
| sodium chloride | 82.85 g |
| sodium bicarbonate | 42.85 g |
| sodium acetate (× 3 H$_2$O) | 3.06 g |

In the final dialysis fluid, i.e. after dilution to the 15-fold of its volume, this basic concentrate supplies:

| | |
|---|---|
| sodium ions | 130 mmol/l |
| chloride ions | 94.5 mmol/l |
| bicarbonate ions | 34 mmol/l |
| acetate ions | 1.5 mmol/l |

Example 1.1:

An appropriate individual concentrate of typical average composition adds to the final dialysis fluid solute components in concentrations indicated in the first column of the folling table, resulting in final or total concentrations in the dialysis fluid according to the second column (in units of mmol/liter):

| | | |
|---|---|---|
| sodium ions | 9 | 139 |
| potassium ions | 2 | 2 |
| calcium ions | 1.65 | 1.65 |
| magnesium ions | 0.5 | 0.5 |
| chloride ions | 17.8 | 112.3 |
| bicarbonate ions | 0 | 34*) |
| acetate ions | 0 | 1.5 |
| Glucose | 5 | 5 |

*)Remark: When bicarbonate from the basic concentrate and acid from the individual concentrate are combined in the dialysis fluid, part of the bicarbonate is transformed to water and carbon dioxide. After equilibration, this results in a slight reduction of the bicarbonate concentration. This is a normal effect in bicarbonate dialysis fluids.

The typical individual concentrate of average composition, as indicated, is adjusted to the requirements of a well-adapted, adult dialysis patient with normal metabolic functions and without any other acute or chronic diseases.

To produce this individual concentrate in the form of a 170-fold liquid concentrate, the following quantities of substances (in g) are dissolved in water to obtain 1 liter of concentrate, sufficient for 170 liters of dialysis fluid:

| | |
|---|---|
| sodium chloride | 89.43 |
| potassium chloride | 25.35 |
| calcium chloride × 6H$_2$O | 61.45 |
| magnesium chloride × 6H$_2$O | 17.28 |
| hydrochloric acid 37% | 42.5 |
| glucose × 1H$_2$O | 168.45 |

Example 1.2:

The data of another individual concentrate, which is intended to be used in combination with the basic concentrate of example 1.0, are indicated in the following table. The first colums shows the concentrations contributed by the individual concentrate, the second column indicates the final or total concentrations in the dialysis fluid (in mmol/liter):

| | | |
|---|---|---|
| sodium ions | 12 | 142 |
| potassium ions | 1 | 1 |
| calcium ions | 1.25 | 1.25 |
| magnesium ions | 0.5 | 0.5 |
| chloride ions | 22 | 116.5 |
| bicarbonate ions | 0 | 34 |
| acetate ions | 0 | 1.5 |
| glucose | 5 | 5 |

This individual concentrate may be suitable for a dialysis patient suffering from renal bone disease in conjunction with secondary hyperparathyroidism, and taking high doses of vitamin D and an oral calcium-based phosphate binder.

To produce this individual concentrate in the form of a 170-fold liquid concentrate, the following quantities of substances (in g) are dissolved in water to obtain 1 liter of concentrate:

| | |
|---|---|
| sodium chloride | 98.20 |
| potassium chloride | 10.44 |
| calcium chloride × 6H$_2$O | 46.56 |
| magnesium chloride × 6H$_2$O | 17.28 |
| hydrochloric acid 37% | 42.5 |
| glucose × 1H$_2$O | 168.45 |

Example 1.3:

The following table, analogous to the previous examples, describes a third individual concentrate which is to be used in combination with the basic concentrate of example 1.0:

| | | |
|---|---|---|
| sodium ions | 5 | 135 |
| potassium ions | 3 | 3 |
| calcium ions | 1.75 | 1.75 |
| magnesium ions | 0.7 | 0.7 |
| chloride ions | 15.9 | 110.4 |
| bicarbonate ions | 0 | 34 |
| acetate ions | 0 | 1,5 |
| glucose | 10 | 10 |

This individual concentrate could be suitable for a dialysis patient suffering from diabetes mellitus and high blood pressure and showing a tendency for cramps.

To produce this as a 170-fold liquid concetrate, the following quantities (in g) are dissolved in water per liter of concentrate:

| | |
|---|---|
| sodium chloride | 49.68 |
| potassium chloride | 38.02 |
| calcium chloride × 6H$_2$O | 65.18 |
| magnesium chloride × 6H$_2$O | 24.20 |
| hydrochloric acid 37% | 51.00 |
| glucose × 1H$_2$O | 336.91 |

Examples 1.4/1.5/1.6:

These are examples of 170-fold liquid concentrates with a very high solute content:

a) Substances dissolved in g/liter of individual concentrate:

| | Example 1.4 | Example 1.5 | Example 1.6 |
|---|---|---|---|
| sodium chloride | 159 | 198.7 | 238.5 |
| potassium chloride | 50.7 | 63.4 | 25.3 |
| calcium chloride | 74.5 | 74.5 | 61.5 |
| magnesium chloride | 34.6 | 34.6 | 17.3 |
| acetic acid | 25.5 | 25.5 | 25.5 |
| glucose | 505.4 | 168.5 | 0 | b) Contribution to the total concentration of the final dialysis fluid (mmol/l):

| | Example 1.4 | Example 1.5 | Example 1.6 |
|---|---|---|---|
| sodium ions | 16 | 20 | 24 |
| potassium ions | 4 | 5 | 2 |
| calcium ions | 2 | 2 | 1.65 |
| magnesium ions | 1 | 1 | 0.5 |
| chloride ions | 26 | 31 | 30.3 |
| aetate ions | 2.5 | 2.5 | 2.5 |
| glucose | 15 | 5 | 0 |

The examples 1.4/1.5/1.6 demonstrate that the composition of 170 liters of dialysis fluid can be varied in surprisingly wide ranges by means of only one liter of individual concentrate.

Even at low temperature (5° C.) these concentrates do not show any precipitation of solutes. This is surprising in view of the fact that, for example, the individual concentrate of example 1.4 (density 1.29 g/ml) contains 0.824 kg of dry substance per liter. Its liquid content of water and acid is only approximately 361 g per kg of concentrate (36.1%).

Except for its normal content of glucose, the individual concentrate of example 1.5 supplies very high concentrations of potassium, calcium, and magnesium ions, which are seldom needed and rarely required in combination. Nevertheless, this concentrate can supply sodium ions in a concentration up to 20 mmol/l in the final dialysis fluid. Starting from the basic concentrate of example 1.0, supplying sodium ions in a concentration of 130 mmol/l, this means that a sodium concentration of 150 mmol/l in the final dialysis fluid is obtained. This possibilty to vary the sodium concentration in the dialysis fluid between 130 and 150 mmol/l is more than sufficient to cover the whole physiological range and even allows sodium profiles to be produced in the ranges that are recommended in the literature.

Example 2.0:

A 16-fold liquid basic concentrate was produced by dissolving in water the following quantities of salts per liter of concentrate:

| | |
|---|---|
| sodium chloride | 92.52 g |
| sodium bicarbonate | 43.69 g |
| sodium acetate (× 3 H$_2$O) | 5.44 g |

In the final dialysis fluid, i.e. after dilution, this basic concentrate supplies:

| | |
|---|---|
| sodium ions | 135 mmol/l |
| chloride ions | 100 mmol/l |
| bicarbonate ions | 32.5 mmol/l |
| acetate ions | 2.5 mmol/l |

Examples 2.1/2.2:

These are examples of 200-fold liquid individual concentrates to be used in conjunction with 16-fold basic concentrate of example 2.0. Example 2.1 represents a concentrate of typical average composition, whereas example 2.2 represents a concentrate with high solute content.

a) Substances dissolved in g/liter of individual concentrate:

| | Example 2.1 | Example 2.2 |
|---|---|---|
| sodium chloride | 46.8 | 116.9 |
| potassium chloride | 29.8 | 74.6 |
| calcium chloride | 72.3 | 87.6 |
| magnesium chloride | 20.3 | 40.7 |
| hydrochloric acid (37%) | 49.3 | 29.6 |

-continued

|  | Example 2.1 | Example 2.2 |
| --- | --- | --- |
| acetic acid (100%) | 0 | 11.8 |
| glucose | 198.2 | 495.5 | b) Contribution to the total concentration of the final dialysis fluid (mmol/l):

|  | Example 2.1 | Example 2.2 |
| --- | --- | --- |
| sodium ions | 4 | 10 |
| potassium ions | 2 | 5 |
| calcium ions | 1.65 | 2 |
| magnesium ions | 0.5 | 1 |
| chloride ions | 10.3 | 22.5 |
| aetate ions | 2.5 | 3.5 |
| glucose | 5 | 12.5 |

A volume of approximately only 0.85 liter of these individual concentrates is needed for the preparation of 170 liters of dialysis fluid. In conjunction with the basic concentrate of example 2.0, the whole physiological range of the main constituents is covered. The sodium concentration may be varied between 135 and 145 mmol/liter, which also corresponds to these requirements. This, however, does not take into account extreme variations that may be desirable for extended sodium profiling.

In the examples 1.0 and 2.0 two different basic concentrates have been indicated, although a main idea of the invention is to apply a uniform or standardized basic concentrate in all cases. These examples, however, were intended to demonstrate that there is some latitude in determining the composition or formulation of the standard basic concentrate.

For the definition of the composition of the basic concentrate the following requirements, some of which are contradictory, have to be considered:

1) maximum range of variability in the composition of the final dialysis fluid within the physiologigal range with preferably a very small voulume of individual concentrate;

2) low volume of basic concentrate if applied as a prefabricated liqid concentrate;

3) high stability and storability;

4) physiologically acceptable low acetate content.

In order to reserve a sufficient range for the physiolgical adptation of the sodium concentration and also to keep the volume of the basic concentrate low, the sodium content of the basic concentrate should not be too high. A preferred sodium concentration should be at, or slightly below, the lower limit of the physiological range, i.e. between 122,5 and 135 mmol/l circa, obtained in the final dialysis fluid. A sodium content lower than this would require a higher quantity of sodium in the individual concentrate. This would increase the volume of the individual concentrate and thus be contrary to another important aspect of the invention.

The requirement for good stability and storability of the basic concentrate (especially at low temperature) can more easily be met by an addition of sodium acetate to the basic concentrate, as experiments have shown. On the other hand, the acetate content of the dialysis fluid should be limited for physiological reasons. Surprisingly, small quantities of acetate in the basic concentrate enhance the solubility of sodium bicarbonate and prevent its precipitation. Presumably this is caused by the formation of complex ions of acetate and bicarbonate. On the basis of experimental results with regard to the solubility of different mixtures of sodium bicarbonate, sodium acetate, and sodium chloride, it may be assumed that in these complex ions acetate and bicarbonate ions are associated in a ratio of 1:3 circa. The increased solubilty of sodium bicarbonate in solutions containing sodium acetate at least corresponds to this hypothesis and the ratio as indicated. It may be that this effect has not been recognized yet or, at least, has not been used to keep the volume of a dialysis concentrate as small as possible.

Figure 1:
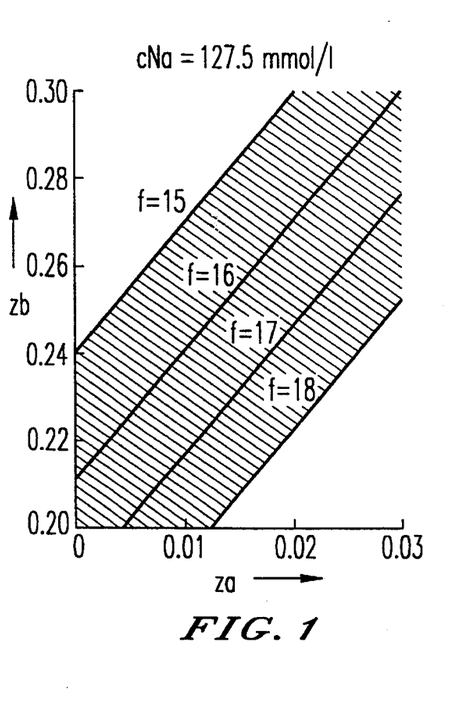
FIGS. 1 to 4 are diagrams representing the ranges of the ratio of solution components in the basic concentrate according to the invention.
Figure 2:
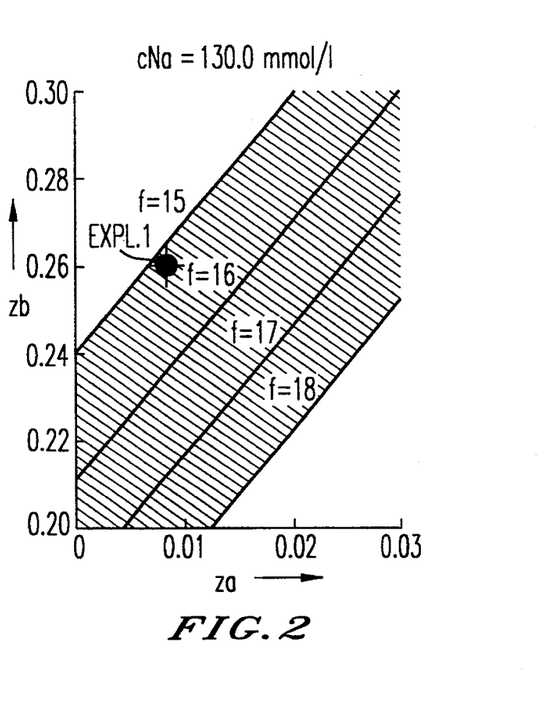
Figure 3:
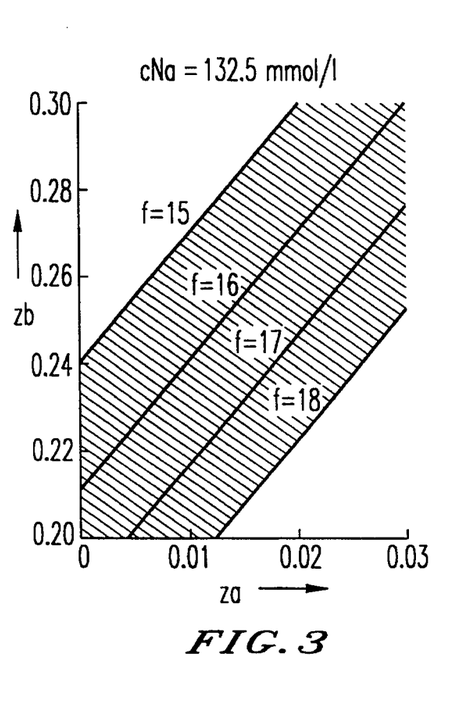
Figure 4:
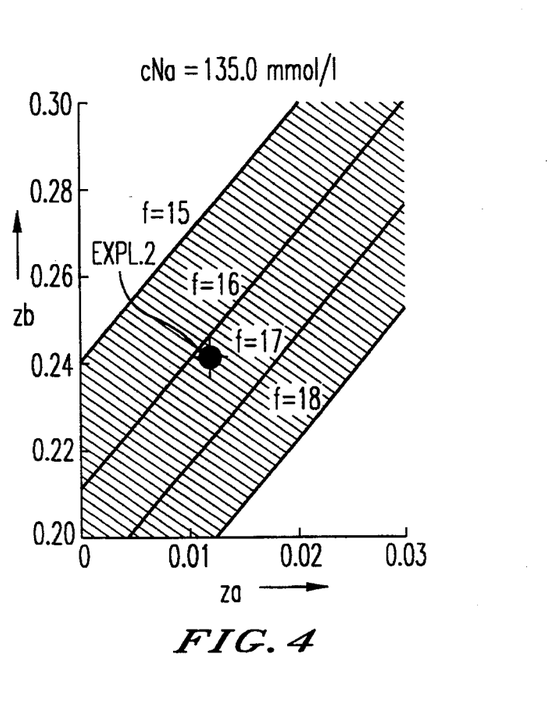

For basic concentrates with different total concentrations of sodium ions (referred to the final dialysis fluid) the diagrams of FIGS. 1–4 indicate the amounts of bicarbonate that can be solved when different quantities of acetate are applied. These diagrams are related to a temperature of 10° C. This is justified by the fact that the concentrated (1-molar) solution of sodium bicarbonate, normaly used for bicarbonate dialysis, is already unstable below 14° C. The quantities za and zb are defined as follows: za is the molar ratio acetate/total sodium; zb is the molar ratio bicarbonate/total sodium. The parameter f represents the concentration factor, identical to the dilution factor that has to be applied when the concentrate is diluted to produce the dialysis fluid. The curves indicate the solubility limit. A mixture of sodium chloride, sodium acetate, and sodium bicarbonate is completely soluble, if the appropriate point lies below the appropriate curve pertaining to the concentration factor f that is applied. Whithout the effect of acetate, as described before, the curves, starting from their intersection with the zb-axis, would remain horizontal. The examples 1.0 an 2.0 are indicated in FIG. 2 und FIG. 4 respectively.

These results, in conjunction with the previous considerations, lead to the following determination of the properties of the basic concentrate (not taking into account the additional solutes supplied by the individual concentrate):

a) concentration of sodium ions, referred to the final dialysis fluid (after dilution): 125–135 mmol/l;

b) molar ratio acetate/sodium: 0–0.03;

c) dilution factor: 15–18;

d) molar ratio bicarbonate/sodium: 0.2–0.35.

Figure 5:
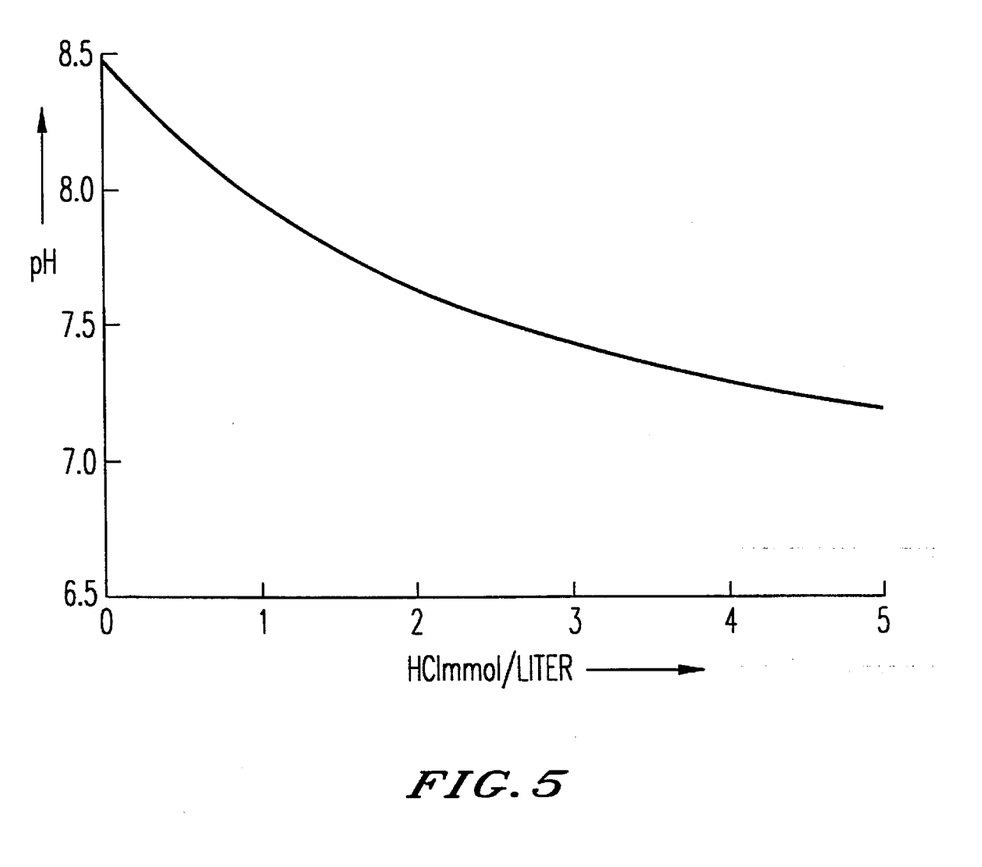
FIG. 5 is a diagram showing the pH of a typical final dialysis fluid as a function of the quantity of hydrochloric acid supplied by the individual concentrate.

The individual concentrates contain a physiologically acceptable acid to reduce the DH of the dialyse fluid to a suitable level. According to the invention, hydrochloric acid is preferred for this purpose, in order to limit the total concentration of acetate in the dialysis fluid to 5 mmol/l circa, including the concentration of acetate from the basic concentrate. The hydrochloric acid may, however, be partially or totally replaced by acetic acid and/or other physiologically acceptable acids, if the limit for the total acetate concentration is not exceeded. The pH value of a dialysis fluid of typical composition, in relation to the addition of hydrochloric acid (in mmol/l, referred to the concentration in the dialysis fluid), is shown in the diagram FIG. 5. Within the realm of measuring error, this curve also applies to acetic acid. The normal range for the acid content is between 2 and 3.5 mmol/l. This quantity may also, in certain cases, be important regarding an individiual adaptation to the physiological requirements of a patient.

According to the invention, the total quantity of individual concentrate required for one dialysis treatment is very small, typically one liter or even less. None of the comparable methods available until now have offered the possibility to vary the concentrations of sodium, potassium, calcium, magnesium, and glucose over the whole physiological range with only such a small volume of concentrate.

The small volume of the individual concentrate also offers the possibility that simple dialysis machines can be used, especially also machines that are only equipped for acetate dialysis, by applying one of the conventional volumetric pumps, that are used as infusion pumps in hospitals, to administrate the individual concentrate. Because of its small volume, the individual concentrate can, for example, be directly administered into the dialisis fluid conduit leading to the dialyzer without the risk of an unacceptable temperature drop. With an initial dialysate fluid temperature of 37° C. and a temperature of the individual concentrate of 20° C. the temperature drops by only 0.1 degree.

In a hospital dialysis unitl the basic concentrate of standardized formulation will preferably be distributed via a central concentrate supply system. The individual concentrates, with regard to their small quantities, can easily be carried to the dialysis machine by the medical personnel, as well as other materials required to perform a dialysis treatment. For the continuous dosing of the individual concentrate into the dialysis circuit a volumetric pump, for example of the usual type of infusion pumps, may be used to feed the individual concentrate into the dialysis fluid circuit upstream from the dialyzer.

The method according to the invention offers important advantages: There is practically no limitation in individually adapting the composition of the dialysis fluid to the requirements of each single patient by selecting a suitable individual concentrate, because the range of variation indicated above covers all these requirements and could even be extended if necessary. The burden of handling, transport, and storage is greatly reduced, in comparison to the problems when using the traditional larger size (e.g. 10 liter) canisters as described. According to the small quantities of individual concentrate applied, the residual quantities of these are much smaller, and also the recycling of the relatively small bottles or bags, similar to those used in infusion therapy, is less problematic.

An important advantage results from the use of a uniform or standardized basic concentrate for the whole range of various compositions of dialysis fluids. Production, distribution, transport, and storage are greatly simplified, which should, accordingly, lead to cost reductions.

Further advantages:

a) When the standardized basic concentrate is to be distributed to several treatment facilities or dialysis machines via a central supply system, only a single tubing system is required, whereas for bicarbonate dialysis, according to the traditional method, a dual tubing system is necessary for the same purpose.

b) Assuming that the small quantity of individual concentrate is continuously added by an infusion pump or a similar external device, the proportioning system of the hemodialysis machine must be capable of dosing only a single concentrate, i.e. the basic concentrate of uniform composition, whereas for bicarbonate dialysis, according to the traditional method, a more complicated dual proportioning system is necessary.

c) Because of its high concentration of sodium chloride, and its higher osmolarity of typically 4000 mosmol/liter circa, the basic concentrate, according to the invention, is less prone to the proliferation of microorganisms than the pure sodium bicarbonate solution, which is used as one of the concentrates in the traditional form of bicarbonate hemodialysis. Therefore, the hygienic problems, normally associated with bicarbonate dialysis, are reduced.

The advantage mentioned above under (b) practically means that existing hemodialysis machines for acetate hemodialysis, having a proportioning system for only a single concentrate, can now, by the addition of relatively simple external equipment, be used for bicarbonate hemodialysis, furthermore taking advantage of the possibility of adapting the fluid composition to the patients' individual requirements.

Figure 6:
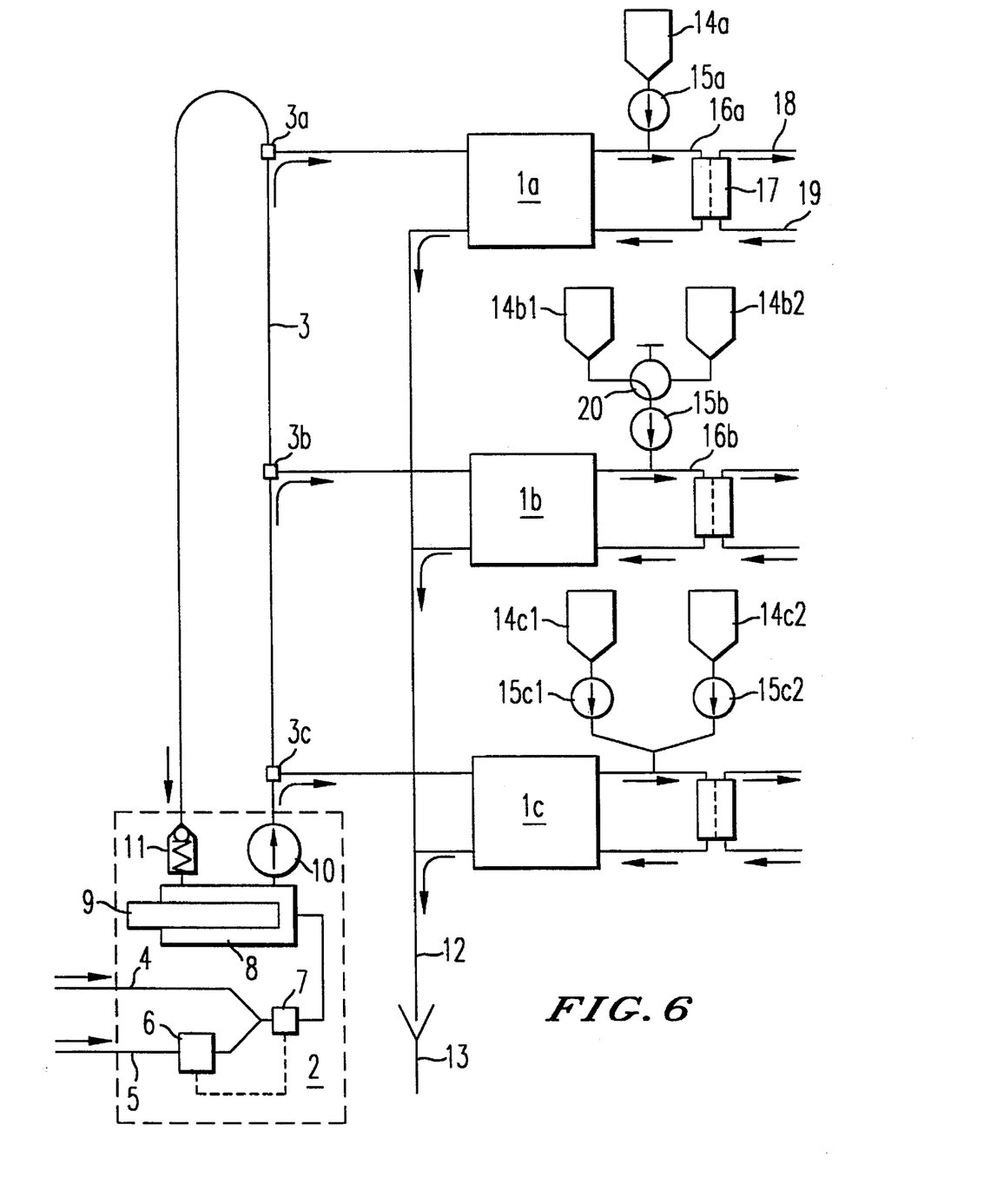
FIG. 6 is a schematic of a circulatory system for supplying a basic concentrate or basic dialysis fluid to several dialysis machines and also illustrates different methods for the administration of the individual concentrates including "profiling" of the dialysis fluids.

In the arrangement of FIG. 6 a central supply unit 2 is applied to distribute a basic concentrate of the composition described in the previous examples, or a corresponding basic dialysis fluid, to several dialysis machines $1a$, $1b$, $1c$ via a ring line 3. This schematic shows only three dialysis machines. An arragement of this type is, however, suitable for a larger number of machines, as required for dialysis units in hospitals.

The internal structure of supply unit 2, shown only in a purely schematical manner, refers to the case of using a liquid basic concentrate, supplied from a reservoir via conduit 5, and pretreated water, for example supplied from a reverse osmosis unit via conduit 4, to form a basic dialysis fluid already diluted to the final concentration. Using a 15-fold basic concentrate, according to example 1.0, approximately 14 unit volumes of water must accordingly be admixed to each unit volume of concentrate to form approximately 15 unit volumes of basic dialysis fluid. The 170-fold individual concentrates are added to this basic dialysis fluid in a later stage. Therefore, instead of 14 unit volumes, the water portion should exactly be 15-1-15/170=13.91 unit volumes, to be quite correct.

The proportioning of water and liquid basic concentrate in the ratio as indicated may be obtained by different technical means, for example dosing pumps operating after a volumetric principle, or applying a closed loop control system based on an analysis of the produced mixture. The latter case is schematically indicated in FIG. 6. The concentration of the basic dialysis fluid obtained by mixing water and the basic concentrate is measured by means of an analyzing device 7 and compared to a standard value, and the operation of concentrate dosing device 6 is controlled to keep the deviation of the measured value from the standard value sufficiently small.

The basic dialysis fluid obtained is conducted into a recirculating circuit, consisting of a vessel 8, Pump 10, ring line 3, and pressure regulating valve 11. Pump 10 feeds the basic dialysis fluid into ring line 3 with connections $3a,b,c$ . . . to the individual dialysis machines. The excess solution, not consumed by the dialysis machines, returns via pressure regulating valve 11 into vessel 8. The pressure regulting valve maintains a constant pressure in the ring line, as required for the supply of fluid to the dialysis machines.

As the proportioning of basic concentrate and water is carried out in the central supply unit, the individual dialysis machines need not be equipped with proportioning systems. This leads to considerable simplification and cost savings. Furthermore, the separate supply system, normally necessary to provide the dialysis machines with pretreated water, is not needed. Also, the heating of the fluid to body temperature may take place in the supply unit, if the the vessel 8 is equipped with a thermostatically controlled heater 9. The heating devices in the individual dialysis machines can then be omitted or replaced by small heaters for temperature correction only. Such a central heating device can advantageously also be used to sterilize the whole ring line with hot water before and after use, eventually including the fluid circuits of the dialysis machines connected to it.

An arrangement according to FIG. 6 is adaptable to serve as a central supply system for the basic concentrate only. The basic concentrate is then administered directly into vessel 8 of supply unit 2. The central proportioning equipment is omitted. The pretreated water is provided to the dialysis machines via a separate ring line. In this case, of course, each dialysis machine must be equipped with its own proportioning system.

FIG. 6 also schematically illustrates different methods for the administration of the individual concentrate. In conjunction with dialysis machine 1a, the individual concentrate is supplied from a container 14a, preferably an infusion bag of typically one liter, via a volumetric pump 15a into conduit 16a, which leads the fresh dialysis fluid to the dialyzer 17. By the addition of the individual concentrate in the correct proportion, e.g. 1 unit volume of individual concentrate per 170 unit volumes of dialysis fluid, the dialysis fluid it adjusted to its final composition, individually adapted to the patient. The dialyzer 17 and its connection lines 18 and 19 to the blood circuit of the patient are arranged in the usual way.

In conjunction with dialysis machine 1b an arrangement for "profiling" of the dialysis fluid is indicated. A profile, i.e. a variation of the dialysis fluid composition with time, is obtained by supplying two different individual concentrates from infusion bags 14b1 and 14b2 into conduit 16b via a regulating device 20 and volumetric pump 15b. The regulating device 20, allowing to set different ratios of flow resistances in its two fluid passages, determines the ratio in which the two concentrates are administered. In the simplest case the regulating device is a three-way valve, allowing to switch between the first and second individual concentrate, thereby producing a profile in steps.

Another method to change the composition of the dialysis fluid gradually, in the sense of a continuous profile, is applied in conjunction with dialysis machine 1c. Two appropriately selected individual concentrates are supplied from infusion bags 14c1 and 14c2 via two volumetric pumps 15c1 and 15c2, the pumping speeds being continuously varied, generally keeping the the sum of the flows of the two individual concentrates constant.

The latter condition, however, need not be adhered to in all cases. It may also, for example, be advantageous to run pump 15c1 at constant speed, whereas the speed of pump 15c2, starting from the same initial value, is linearly reduced to zero in the course of a dialysis session.

This is illustrated by the following example, where the following conditions are assumed: Using the basic concentrate of example 1.0, the concentrations of the dialysis fluid components (in mmol/l) are to be varied in the course of a dialysis session as follows:

| | |
|---|---|
| sodium ions | 145 decreasing to 135 |
| potassium ions | 4 decreasing to 1 |
| calcium ions | 1.65 constant |
| magnesium ions | 0.5 constant |
| glucose | 10 decreasing to 5 |

This can be achieved using the following individual concentrates (concentrations in mmol/l, referred to the final dialysis fluid):

| | concentrate 1 | concentrate 2 |
|---|---|---|
| sodium ions | 5 | 5 |
| potassium ions | 1 | 3 |
| calcium ions | 1.65 | 0 |
| magnesium ions | 0.5 | 0 |
| chloride ions | 12.8 | 8 |
| glucose | 5 | 5 |

Concentrate 1 is a "normal" individual concentrate in the sense that it i.a. supplies the acid for pH adjustment (in thsis case: 2.5 mmol HCl per Liter of the final dialysis fluid). Concentrate 2 is an additional acid-free concentrate only for the adjustment of the profile and thus only intended to be used in conjunction with a normal individual concentrate.

During the whole dialysis session concentrate 1 is administered via pump 15c1 at constant speed, whereas the pump 15c2, supplying concentrate 2, starts with the same speed, but reduces its speed linearly to zero in the course of the dialysis session. As a result, taking into account all components of the dialysis fluid, the concentraions vary as follows:

| | |
|---|---|
| sodium ions | 145 decreasing to 135 |
| potassium ions | 4 decreasing to 1 |
| calcium ions | 1.65 |
| magnesium ions | 0.5 |
| chloride ions | 115.3 decreasing to 107.3 |
| bicarbonate ions | 34 |
| acetate ions | 1.5 |
| glucose | 10 decreasing to 5 |

Another aspect of the invention resides in the possibility to produce the basic concentrate at the location of its use, e.g. in a hospital, by dissolving its dry substances in water.

Figure 7:
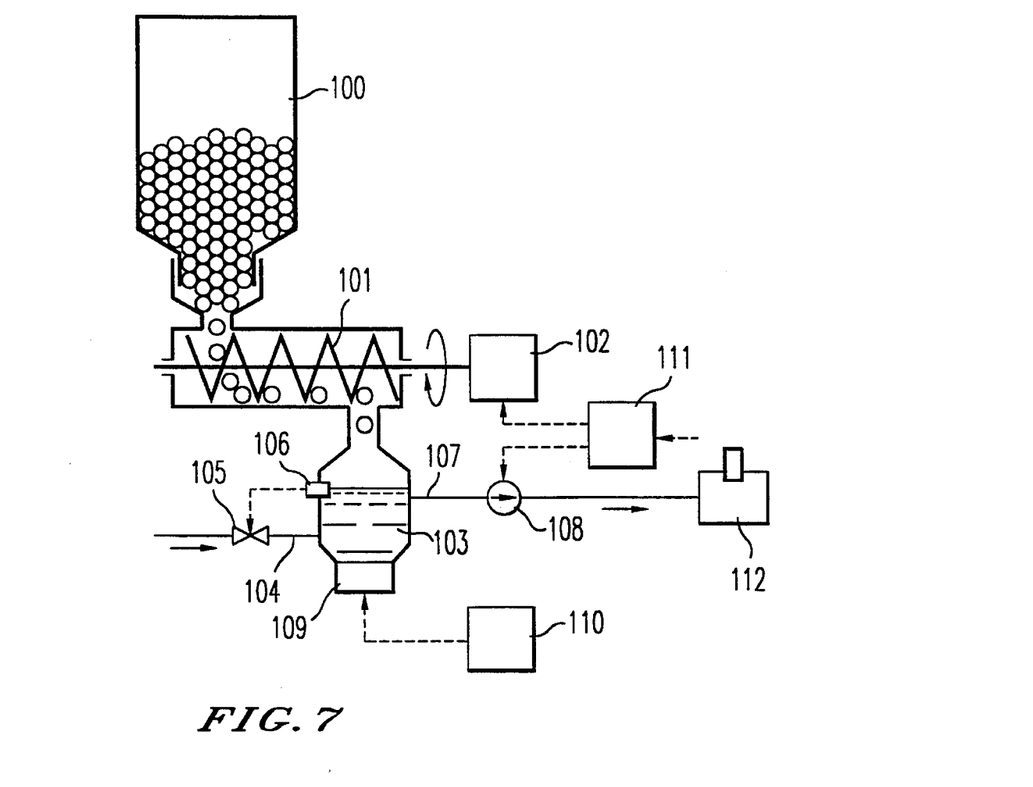
FIG. 7 is a schematic of a circulatory system for the continuous preparation of the basic concentrate or dialysis fluid solution from dry substances.

An embodiment of the invention for this purpose is illustrated in FIG. 7. A homogeneous mixture of the respective salts, shaped to granules or tablets, is applied as a "dry concentrate". The granules or tablets are supplied from container 100 via a mechanical transport and dosing device 101, for example using a worm driven by motor 102, into a chamber 103, where they are dissolved in water. Water enters the chamber via conduit 104, if valve 105 is open. Valve 105 is controlled by level sensor 106 in order to keep the fluid level in the chamber 103 approximately constant. The solution formed, a liqid basic concentrate, is withdrawn from the chamber by pump 108 via conduit 107 and may be used, for example, to feed a tubing system for the central supply of basic concentrate to several hemodialysis machines in a hospital. The arrangement of FIG. 7 could also be part of a single hemodialysis machine, replacing the traditional types of proportioning systems. In order to produce a liqid of constant concentration, a conductivity control system is suitable. A control unit 111 measures the actual conductivity of the liquid by means of sensor 112 and coordinates the speeds of pump 108 and transport mechanism 101,102 to keep the conductivity within a selected range.

With regard to the different speeds at which the substances contained in the particles of the dry concentrate dissolve, and in order to obtain a homogeneos solution with the presribed ratio of its constituents, it has been found that (a) the total solute content of the fluid contained in the chamber 103 should be considerably higher than the solute content of one dosing unit (i.e. one granule or tablet) of the solid concentrate added at a time, and (b) the dissolving speed should be high enough to prevent the accumulation of undissolved substance in the chamber 103. This can be achieved by selecting an appropriate chamber volume and increasing the dissolving speed, preferrably by the application of ultrasound. For the latter purpose the chamber has an ultrasonic transducer 109 fixed to its bottom and connected to a high frequency power generator 110.

Figure 8:
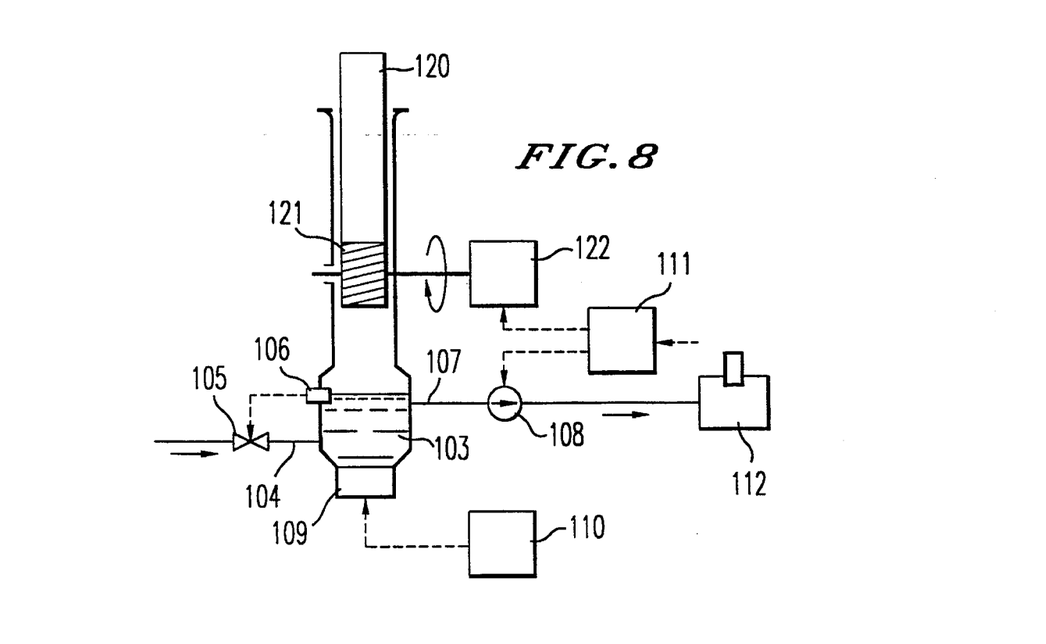
FIG. 8 schematically illustrates another method of continuous preparation of the basic concentrate or fluid from its dry substance.

Another similarly advantageous embodiment of the invention is to apply a solid basic concentrate in the form of prefabricated rod-shaped or similar pieces of material, for example in a size according to the quantity for one dialysis treatment, i.e. approximately 1 kg, produced by pressing or extruding a homogeneous mixture of the pulverized salts with the addition of a physiologically acceptable binding material as required (for example gelatine, polyvinyl pyrrolidone, or polysaccharides). According to this embodiment, the prefabricated pieces of solid basic concentrate, at the time and location of use, are mechanically crushed or pulverized in a continuous process and the substance dissolved in a flowing stream of water in order to prepare the liquid basic concentrate. An arrangement for this purpose is illustrated in FIG. 8. The rod-shaped piece 120 of solid concentrate is ground using a fluted roller 121, the powder formed falling into the chamber 103. The other elements indicated perform the same functions as in FIG. 7.

The addition of water required to form the solution is preferably controlled by measuring the conductivity of the solution using a closed loop conductivity control system. Similar to the application of the prefabricated liquid basic concentrate, with an approriate selection of the conductivity level a liquid basic concentrate can be formed and supplied to the dialysis machines and then diluted to the final concentration by the addition of water. With a different setting of the conductivity level, corresponding to the addition of an increased proportion of water in the dissolving process, it is also possible to produce a basic dialysis fluid of final concentration directly, requiring only the addition of the individual concentrate to obtain the dialysis fluid ready for use, as explained in conjunction with FIG. 6.

I claim:

1. A method for preparing a bicarbonate hemodialysis fluid adapted to the individual physiological requirements of a patient in need of dialysis, comprising the steps:
   i) providing a primary concentrate (a) of fixed concentration and not tailored to the individual physiological requirements of the patient,
   ii) providing a plurality of additional concentrates (b) having differing compositions,
   iii) selecting a concentrate (b) according to the individual physiological requirements of the patient, and
   iv) diluting concentrate (a) and the selected concentrate (b) with water to obtain said hemodialysis fluid; wherein
      primary concentrate (a) supplies sodium ions between 120 and 135 mmol/liter based on the hemodialysis fluid, 100% of the bicarbonate and has a molar ratio of bicarbonate/sodium of 0.3 or less; and
      concentrate (b) is a 120 to 250-fold liquid concentrate that supplies additional sodium in an amount up to 25 mmol/l, 0–5 mmol/l potassium, 0.3–2.5 mmol/l calcium and 0–1.2 mmol/l magnesium ions, all concentrations based on said hemodialysis fluid, representing the total quantities of calcium and magnesium ions in the hemodialysis fluid.

2. The method of claim 1, wherein concentrate (b) further comprises glucose in a concentration up to 10 mmol/l.

3. The method of claim 1, wherein concentrate (b) further comprises hydrochloric acid in a concentration up to 4 mmol/l.

4. The method of claim 1, wherein concentrate (a) further comprises acetate ions up to a molar ratio of acetate/sodium of 0.03 and being a 15 to 18-fold liquid concentrate.

5. The method according to claim 1, wherein concentrate (a) consists of two separate liquid components.

6. The method according to claim 1, wherein concentrate (a) is formed from a dry substance in an intermediate step of the dilution process, forming an at least 5-fold liquid concentrate.

7. The method of claim 1, wherein concentrate (a) is formed from a dry substance, the dry substance being dissolved and diluted with water in a proportion corresponding to the final concentration of said hemodialysis fluid.

8. The method of claim 7 or claim 6, wherein the dry substance of concentrate (a) is applied in prefabricated pieces of standardized geometric shape and size, the pieces of dry concentrate being pulverized in a continuous process and the pulverized substance being dissolved in a flowing stream of water.

9. The method of claim 1, wherein concentrate (a) is diluted with water to the final concentration and distributed to several dialysis machines from a central supply system.

10. The method of claim 1, wherein concentrate (b) is continuously dosed into a flowing stream of diluted concentrate (a).

11. The method of claim 1, wherein a solution is formed by continuously dosing concentrate (b) into a flowing stream of water in a predetermined first proportion and concentrate (a) is continuously added to that solution in a predetermined second proportion.

12. The method according to claim 11, wherein concentrate (b) is dosed into the water supply conduit of a hemodialysis machine.

13. The method of claim 1, wherein more than one concentrate (b) is applied in parallel or in a sequence.

14. The method of claim 1, wherein said concentrate (a) supplies at least 90% of the total solute content of said hemodialysis fluid and has a molar ratio of bicarbonate/sodium of 0.27 or less.

* * * * *